US00PP33277P2

(12) United States Plant Patent
Hansen

(10) Patent No.: US PP33,277 P2
(45) Date of Patent: Jul. 20, 2021

(54) ***HOSTA* PLANT NAMED 'PARTY STREAMERS'**

(50) Latin Name: ***Hosta* hybrid**
Varietal Denomination: Party Streamers

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,299

(22) Filed: Dec. 18, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

(56) References Cited

PUBLICATIONS http://www.plantsgalore.com/Hostas/cultivars/P/Hosta_Party_Streamers.htm (Retrieved from Internet on Apr. 1, 2021—3 pages total).*

* cited by examiner

*Primary Examiner* — Susan McCormick Ewoldt

(57) ABSTRACT

A new and distinct *Hosta* plant named 'Party Streamers' with medium, rounded-mound habit of arching chartreuse foliage. Leaves are long and narrow with wavy margins. Flowering begins in late July through late August with tepals opening wide to show strong violet coloration with darker veins. Seed pods take on purplish-red coloration when developing in high light conditions. The new plant is attractive for landscaping in the garden as a specimen, in mass and as a container.

2 Drawing Sheets

Latin name and variety denomination of the plant:
Botanical classification: *Hosta* hybrid.
Variety denomination: 'Party Streamers'.

STATEMENT REGARDING PRIOR DISCLOSURES UNDER 37 CFR 1.77(B)(6)

*Hosta* 'Party Streamers' was first introduced by the inventor as a non-enabling description through the International Cultivar Registration Authority registration in early 2020. No plants of *Hosta* 'Party Streamers' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Party Streamers' hereinafter also referred to as the new plant or just the cultivar name, 'Party Streamers'. *Hosta* 'Party Streamers' was single seedling selection from a cross on Aug. 23, 2013 by the inventor at a wholesale perennial nursery in Zeeland, Mich., USA between 'Atom Smasher' (not patented) as the female parent and the non-patented, unreleased, proprietary hybrid known only as '11-463-02' (not patented) as the male parent. The new plant was assigned the breeder code 13-443-4 and passed the initial evaluation in the summer of 2016. The new plant has been asexually propagated by division at the same nursery in Zeeland, Mich., USA since 2017 and also by careful plant shoot-tip tissue culture with the resultant asexually propagated plants having retained all the same traits as the original plant.

BRIEF SUMMARY OF THE PLANT

There are over 7,000 registered and unregistered *Hosta* cultivars recognized by The American *Hosta* Society, which is the International Cultivar Registration Authority for the genus *Hosta*. The nearest known comparison cultivars are the female parent, 'Atom Smasher', 'Bitsy Gold' (not patented), 'Cricket' (not patented), 'Curly Fries' (not patented), 'Munchkin Fire' (not patented), 'Pineapple Juice' (not patented), 'Surfer Girl' (not patented) and 'Wiggles and Squiggles' (not patented).

All of the above plants have a lanceolate leaves with undulate margins. 'Atom Smasher' is smaller in height, the foliage is less arching, and the flowers are not as purple. 'Bitsy Gold' is smaller in habit, with smaller foliage that is more yellowish and lacks the undulation. 'Cricket' is about half the size in habit with smaller foliage that has a cordate base, and the proportion of blade width to length is greater. 'Curly Fries' has a larger habit with smaller, longer and narrow leaves with less reddish stippling in the petiole and the undulation decreases with maturity. 'Munchkin Fire' has a smaller habit with smaller shorter leaves that are more yellowish. 'Pineapple Juice' has a larger habit, but the growth rate is slower, the foliage is lighter yellow, and the petiole has much less reddish stippling. 'Surfer Girl' has smaller habit with shorter foliage that has a cordate base and the flowers are paler purple. 'Wiggles and Squiggles' has a larger habit, the foliage is lighter yellow with less reddish stippling in the petiole and flower scape.

The male parent was less yellowish in foliage and had a larger habit.

Other *Hosta* cultivars have similar colored foliage, but 'Party Streamers' is distinct from the above listed *Hostas* and all other cultivars known to the discoverer by the following combined traits:

1. Medium-sized, round-mounded plant habit with arching chartreuse foliage;
2. Leaves are long and narrow with wavy margins;
3. Medium-sized flowers droop downwardly from erect scapes well above the foliage;
4. Tepals are strong violet with darker veins and vitreous or transparent margins.
5. Seed pods display a purplish-red while developing.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
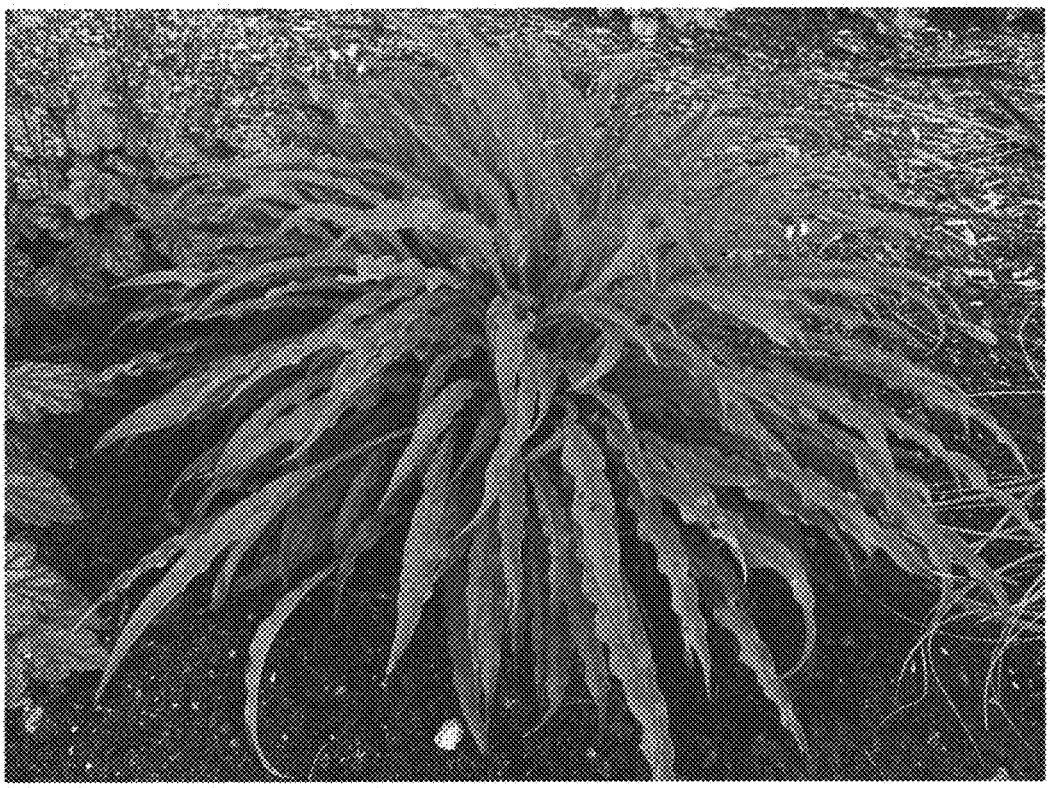
FIG. 1 shows the habit of a five-year-old plant in mid-season.
Figure 2:
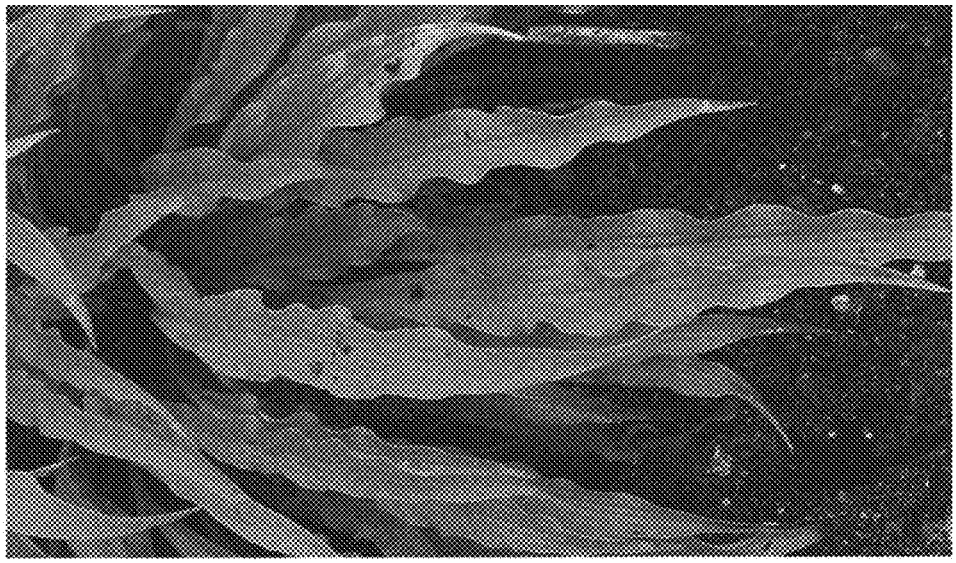
FIG. 2 shows a close-up of the foliage.
Figure 3:
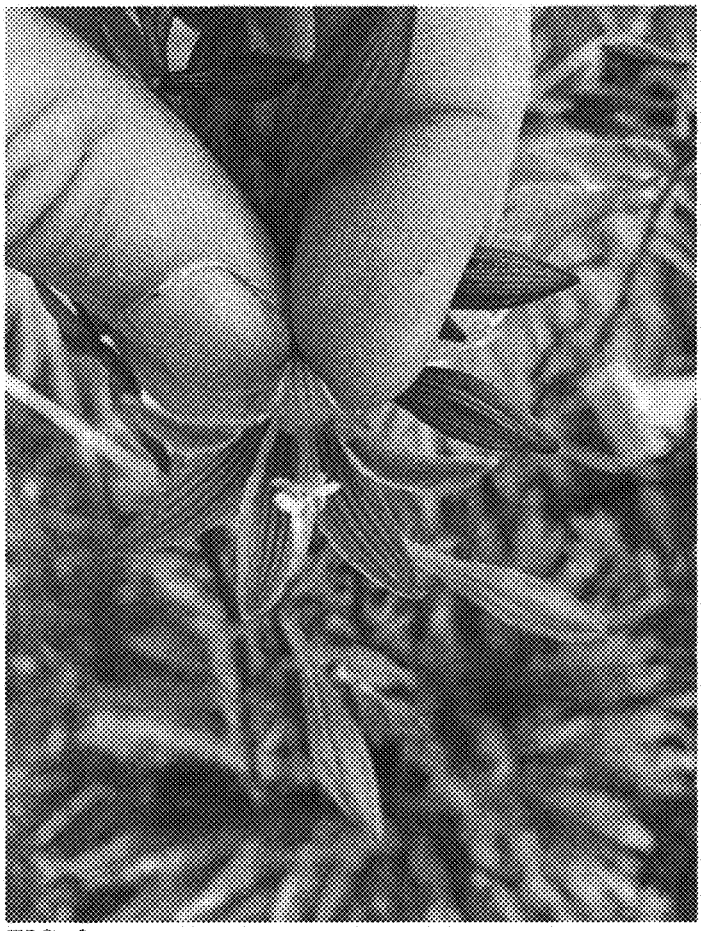
FIG. 3 shows a close-up of a flower and buds.

The following descriptions and color references are based on the 2015 edition of The Royal Horticultural Society Colour Chart except where common dictionary terms are used. The new plant, *Hosta* 'Party Streamers', has not been observed under all possible environments. The phenotype may vary slightly with different environmental conditions, such as temperature, light, fertility, moisture and maturity levels, but without any change in the genotype. The following observations and size descriptions are of a seven-year old plant in a partially shaded trial garden in Zeeland, Mich. with supplemental water and fertilizer.

Botanical classification: *Hosta* hybrid;

Parentage: 'Atom Smasher' as the female parent, and '11-463-2' as the male parent which has in its background 'Curly Fries' (not patented) and 'Mason Yellow' (not patented);

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color between RHS NN155A and RHS NN155B;

Plant shape and habit: Hardy herbaceous perennial with basal rosettes of leaves emerging from rhizomes producing a large, symmetrical, rounded-mound of leaves; about 28 divisions per plant; divisions to about 6.0 mm diameter at soil level;

Plant size: Foliage height about 30.5 cm above soil line to the top of the leaves and about 78.7 cm wide at the widest point about 20 cm at soil line;

Foliage description: Lanceolate to linear; narrowly acute apex; attenuate base; entire undulate margin; glabrous and matte adaxial, glabrous and lustrous abaxial; blades mostly flat in center with margin undulate; flexible; not variegated;

Leaf blade size: To about 15.2 cm long, 2.5 cm wide at base; average about 13.0 cm long and 1.8 cm wide;

Leaf blade color: Early season and expanding adaxial nearest RHS N144D, early season and expanding abaxial nearest RHS N144D; mid-season and later summer adaxial nearest RHS N144D in higher sunlight exposure and nearest RHS 144A in lower sunlight or more shaded exposure; mid-season and later abaxial between RHS 144A in lower sunlight exposure and RHS N144D in higher sunlight exposure;

Petiole: Entire, glabrous, moderately concavo-convex; flexible; slightly arching from base of plant to leaf base; to about 11.0 cm long and 3.0 mm wide at base and 3 mm deep;

Petiole color: Young early season adaxial and abaxial between RHS 150B and RHS 150C with proximal one-third heavily maculate with nearest RHS N79C, mature adaxial nearest RHS 146B maculate with nearest RHS 187C, mature abaxial nearest RHS 146C heavily maculate in proximal three-quarters with nearest RHS 187DD;

Veins: Parallel, lightly impressed adaxial, moderately costate and smooth abaxial; about 5 to 6 pairs and one main center vein;

Veins color: Adaxial and abaxial same as surrounding tissue with light exposure;

Flower description: Perfect; single; actinomorphic; funnel-form, flared campanulate; slightly drooping; persist for normal period, usually one day on plant or as cut flower;

Flower period: Scapes remain effective with flowering beginning late July through late August in Michigan;

Inflorescence: Strongly secund; flowering in distal 18.0 cm and about 6.0 cm wide; with up to 14 flowers per inflorescence;

Flower size: About 51.0 mm long to exserted style; corolla to about 45.0 mm long and flared to about 45.0 mm across; corolla tube to about 18.0 mm long and 3.0 mm diameter toward base; Fragrance: none detected;

Scape bracts: Typically 4, rarely 5 per scape below flowers; lanceolate; narrowly acute apex, clasping truncate base, entire margin; to about 30.0 mm long and 8.5 mm across near middle, decreasing distally;

Scape bract color: Adaxial longitudinal center nearest RHS 146D in basal three-quarters, distal one-quarter and margins nearest RHS 150D; abaxial basal two-thirds nearest RHS 146D and distal one-third nearest RHS 150D, with basal 3.0 mm heavily spotted with nearest RHS 187C;

Floral bracts: Subtending individual flowers; lanceolate; narrowly acute apex, truncate clasping base, margin entire; glabrous adaxial and abaxial; persistent; to about 20.0 mm long and 7.5 mm across, decreasing in size distally;

Bract color: Adaxial margin nearest RHS 150D, center nearest RHS 145A; abaxial margin RHS 150D, center between RHS 145A and RHS 146D, with adaxial and abaxial veins of nearest RHS 187B;

Tepals: Two sets of three; lanceolate with acute apex and fused base;

*Inner set.*—47.0 mm long and 8.0 mm across slightly above fusion; fused in basal 26.5 mm and free in distal 22.0 mm; vitreous along 1.0 mm wide distal margin.

*Inner set color*.—Adaxial including corolla tube nearest RHS 86D with veins nearest RHS 86A, proximal margins before fusion nearest RHS 84D, fused margins nearest RHS NN155D; abaxial including corolla tube nearest RHS N87D with veins between RHS 86A and RHS 86B, margins between RHS 84D distally, and proximally nearest RHS 84D.

*Outer tepal*.—47.0 mm long and 8.0 mm across slightly above fusion; fused in basal 26.5 mm and free in distal 22.0 mm; not vitreous along margin.

*Outer tepal color*.—Adaxial including corolla tube nearest RHS 86D with veins nearest RHS 86A, proximal margins before fusion nearest RHS 84D, fused margins nearest RHS NN155D; abaxial including corolla tube nearest RHS N87D with veins between RHS 86A and RHS 86B, margins.

Gynoecium: single; tri-carpelled; 51.0 mm long;

*Style*.—Single; cylindrical; arcuate upward about 90° in distal 10 mm; about 46.0 mm long and 1.0 mm diameter; color nearest RHS 145D distally and nearest RHS 145C proximally.

*Stigma*.—Tri-lobed, micro-puberulent; about 1.0 mm across and 1.0 mm tall; color nearest RHS 157C.

*Ovary*.—Superior; ellipsoidal; rounded apex and truncate base; shallowly longitudinally sulcate; about 4.0 mm long and 2.2 mm diameter; color between RHS 146D and RHS 145A.

Androecium: Six;

*Filaments*.—Cylindrical; glabrous; arcuate upward about 90° in distal 5.0 mm portion; about 40.0 mm long and 0.5 mm diameter; color distally nearest RHS NN155D, proximally nearest RHS 155B.

*Anthers*.—Oblong; dorsifixed, longitudinally dehiscent; about 4.0 mm long and 1.5 mm across and 1.5 mm thick; color adaxial variable nearest RHS 166A near center and between RHS 18A and RHS 18B outside, abaxial nearest RHS 18B.

*Pollen*.—Smaller than 0.1 mm diameter; color nearest RHS 17A.

Flower bud: Oblong clavate; with acute apex and fused tubular base; about 45.0 mm long in total and 12.0 mm wide in bulb portion, tube about 14.0 mm long and 3.0 mm diameter;

Flower bud color: Between RHS 85C and N87D with veins nearest RHS 83A;

Pedicel: Cylindrical, glabrous, lustrous; arcuate upwardly and outwardly; to about 9.0 mm long and 1.2 mm diameter;

Pedicel color: Nearest RHS 155A with nearly solid speculate nearest RHS 187C;

Peduncle: Cylindrical; usually one per mature division and 28 per plant; slightly lustrous; glabrous; flexible; nearly upwardly with slight outwardly angle; to about 79.0 cm long and about 3.0 mm diameter;

Peduncle color: When flowering basal 3.0 cm nearly solidly maculate with nearest RHS 187C, middle one-half nearest RHS 146D and moderately maculate nearest RHS 187C, distal portion nearest RHS N144A and maculate nearly solidly with nearest RHS 187C;

Fruit: Tri-valved dehiscent capsule; ellipsoidal to cylindrical with apiculate apex and truncate base; about 22.0 mm long and 5.0 mm diameter; lustrous as maturing;

Fruit color: As maturing nearest RHS 146C to solid RHS N186C with high light exposure; maturing to nearest RHS 164C;

Seed: Typically about 27 per capsule; endospermic; flattened-ellipsoidal wing surrounding embryo at one end of ellipse; to about 9.0 mm long, 3.5 mm wide and 1.0 mm thick at embryo; Seed color: nearest RHS 202A;

Disease tolerance and resistance: The new plant has not shown any resistance to pests and diseases common to *Hostas;*

Growth conditions: The plant grows best and shows best coloration with plenty of moisture, adequate drainage and light shade, but is able to tolerate some drought when mature. Hardiness at least from USDA zone 3 through 9, and other disease resistance is typical of that of other *Hostas.*

It is claimed:

1. A new and distinct ornamental plant cultivar named *Hosta* 'Party Streamers' as herein described and illustrated.

* * * * *